(12) United States Patent
Underwood et al.

(10) Patent No.: US 10,688,003 B2
(45) Date of Patent: Jun. 23, 2020

(54) MICRO-ENVIRONMENT MODULE ARCHITECTURE FOR INFANT CARE DEVICES

(71) Applicant: General Electric Company, Schenectady, NY (US)

(72) Inventors: Thomas Charles Underwood, Laurel, MD (US); James Patrick Cipriano, Laurel, MD (US); Steven Mitchell Falk, Laurel, MD (US); Harry Edward Belsinger, Jr., Laurel, MD (US)

(73) Assignee: General Electric Company, Schenectady, NY (US)

( * ) Notice: Subject to any disclaimer, the term of this patent is extended or adjusted under 35 U.S.C. 154(b) by 546 days.

(21) Appl. No.: 15/384,574

(22) Filed: Dec. 20, 2016

(65) Prior Publication Data

US 2018/0168903 A1    Jun. 21, 2018

(51) Int. Cl.
*A61G 11/00*    (2006.01)
*H04L 29/08*    (2006.01)
(Continued)

(52) U.S. Cl.
CPC ........ *A61G 11/009* (2013.01); *A61B 5/02055* (2013.01); *A61G 11/007* (2013.01); *G16H 40/63* (2018.01); *H04L 12/40019* (2013.01); *H04L 12/40045* (2013.01); *H04L 67/12* (2013.01); *A61G 2203/16* (2013.01); *A61G 2203/20* (2013.01); *A61G 2203/46* (2013.01); *A61G 2210/90* (2013.01); *H04L 12/40182* (2013.01); *H04L 2012/40215* (2013.01); *H04L 2012/40234* (2013.01)

(58) Field of Classification Search
CPC .... A61G 11/009; A61G 11/007; G16H 40/63; A61B 5/02055; G06F 19/3418; H04L 12/40019; H04L 12/40045; H04L 67/12
See application file for complete search history.

(56) References Cited

U.S. PATENT DOCUMENTS 8,795,151 B2    8/2014  Falk et al.
9,198,816 B2    12/2015  Cipriano
(Continued)

*Primary Examiner* — Tim T Vo
*Assistant Examiner* — Phong H Dang
(74) *Attorney, Agent, or Firm* — Andrus Intellectual Property Law, LLP

(57) ABSTRACT

An infant care station that includes multiple operational modules that communicate with each other to carry out the infant care station functions. The multiple modules form part of a micro-environmental platform that allows for communication and power connections between all of the operational components required within the infant care station. The multiple modules communicate with each other utilizing a universal interface bus that includes power connections, communication connections and control connections between the multiple modules. Sensor data obtained by various sensors is stored using a standard data format. A data repository is included in one of the modules and is used to store sensor data obtained from the infant patient, operational protocols and other information needed to operate the infant care station. The data repository provides a central location for both data producers and data subscribers that are part of the micro-environment platform.

14 Claims, 9 Drawing Sheets

(51) Int. Cl.
  *H04L 12/40*    (2006.01)
  *G16H 40/63*    (2018.01)
  *A61B 5/0205*   (2006.01)

(56) References Cited

U.S. PATENT DOCUMENTS

| | | | |
|---|---|---|---|
| 2005/0215844 A1* | 9/2005 | Ten Eyck | A61B 5/02055 600/22 |
| 2010/0231421 A1* | 9/2010 | Rawls-Meehan | A47C 20/041 341/20 |
| 2011/0077473 A1* | 3/2011 | Lisogurski | A61B 5/14551 600/301 |
| 2012/0184120 A1* | 7/2012 | Basta | A61B 5/746 439/213 |
| 2012/0256749 A1* | 10/2012 | Rao | A61B 5/0022 340/573.1 |
| 2013/0141247 A1* | 6/2013 | Ricci | H04W 4/90 340/870.01 |
| 2013/0158339 A1* | 6/2013 | Cipriano | A61G 11/009 600/22 |

* cited by examiner

MICRO-ENVIRONMENT MODULE ARCHITECTURE FOR INFANT CARE DEVICES

BACKGROUND

The present disclosure generally relates to an infant care system, such an incubator, infant warmer or hybrid device. More specifically, the present disclosure relates to a micro-environment platform that includes a plurality of modules that communicate with each other to carry out all of the functions required by the infant care system.

Prematurely born infants require specialized treatment and care due to their small size and still-developing organs and physiological systems. After being born, premature infants are typically placed in devices that create a carefully controlled micro-environment around the patient. The infant care station operates to control environmental conditions of the micro-environment, such as oxygen concentration, temperature, humidity and light in such a manner as to promote the health and well-being of the infant patient.

One type of infant care station is generally referred to as an incubator in which the patient is placed within a physical enclosure and the temperature within the enclosure is carefully controlled with convective heating provided by a forced flow of heated air into the enclosure. Within the micro-environment, the oxygen concentration and humidity can also be accurately controlled.

Another type of infant care station is referred to as a radiant warmer. The radiant infant warmer has an overhead canopy with heating elements that produce radiant heat directed downward onto the infant patient to maintain the temperature of the infant patient.

Hybrid systems are another type of infant care station that incorporates both convective heating systems and radiant heating systems.

Infant care stations typically have multiple operational elements that must be accurately controlled to maintain the micro-environment at desired levels. Further, the infant care station includes one or more displays that provide information to the treating clinician. The infant care station can also have multiple input devices that allow the clinician to control parameters and physical conditions of the infant care station. Each of these systems needs to be accurately controlled and the infant care station can have different combinations of elements being controlled. Therefore, a need exists for a platform and system that can coordinate the multiple functions of the infant care station in a manner to increase scalability and upgradeability.

SUMMARY

The present disclosure relates to an infant care station that creates a micro-environment for an infant patient. The micro-environment region is located around the infant patient and is controlled by the infant care station.

The infant care station includes multiple modules that communicate to each other over a universal interface bus. The universal interface bus includes at least a power line, a high priority communication bus and a low priority communication bus. The universal interface bus allows the plurality of modules to communicate with each other utilizing a common communication protocol and to operate off of a uniform power supply.

In one embodiment of the disclosure, the infant care station includes an interface module, a sensor module and a master module that coordinate with each other to carry out all of the functions required by the infant care station. The interface module includes at least one processor and is configured to operate a display. The interface module receives user inputs from various different components and is operable to drive various outputs, including the display screen and alarm indicators.

In one embodiment of the disclosure, the infant care station includes at least one sensor module that receives at least one sensor input from at least one sensor that is positioned to detect at least one parameter that is related to either the infant patient or the micro-environment. The sensor module can include multiple sensor inputs to monitor both the patient and the micro-environment. The sensor module formats the sensor input information utilizing a standard data format.

The infant care station can further include a master module that controls the supply of electric power to power consuming devices in the infant care station. These power consuming devices can be heaters, fans, motors, humidifiers and servos used to carry out the desired functions of the infant care station. The master module is connected to an input power source and conditions the input power source to create a main DC power supply line. The universal interface bus also includes a low voltage standby power supply line.

In one embodiment of the disclosure, the high priority communication bus of the universal interface bus is a CAN line. The low priority communication bus of the universal interface bus is an LIN bus while the power line of the universal interface bus includes both a main DC voltage power supply line and a low voltage standby power supply line.

In a further embodiment of the infant care station, the infant care station includes a data repository that is contained on one of the modules. The data repository receives and stores at least the sensor input signals such that the interface module, the sensor module and a master module can access the stored information on the data repository through the universal interface bus. The data repository can further include operational algorithms, control parameters, alarm parameters and other data points used to control the operation of the infant care station.

Various other features, objects and advantages of the invention will be made apparent from the following description taken together with the drawings.

BRIEF DESCRIPTION OF THE DRAWINGS

The drawings illustrate the best mode presently contemplated of carrying out the disclosure. In the drawings.

DETAILED DESCRIPTION

Figure 1:
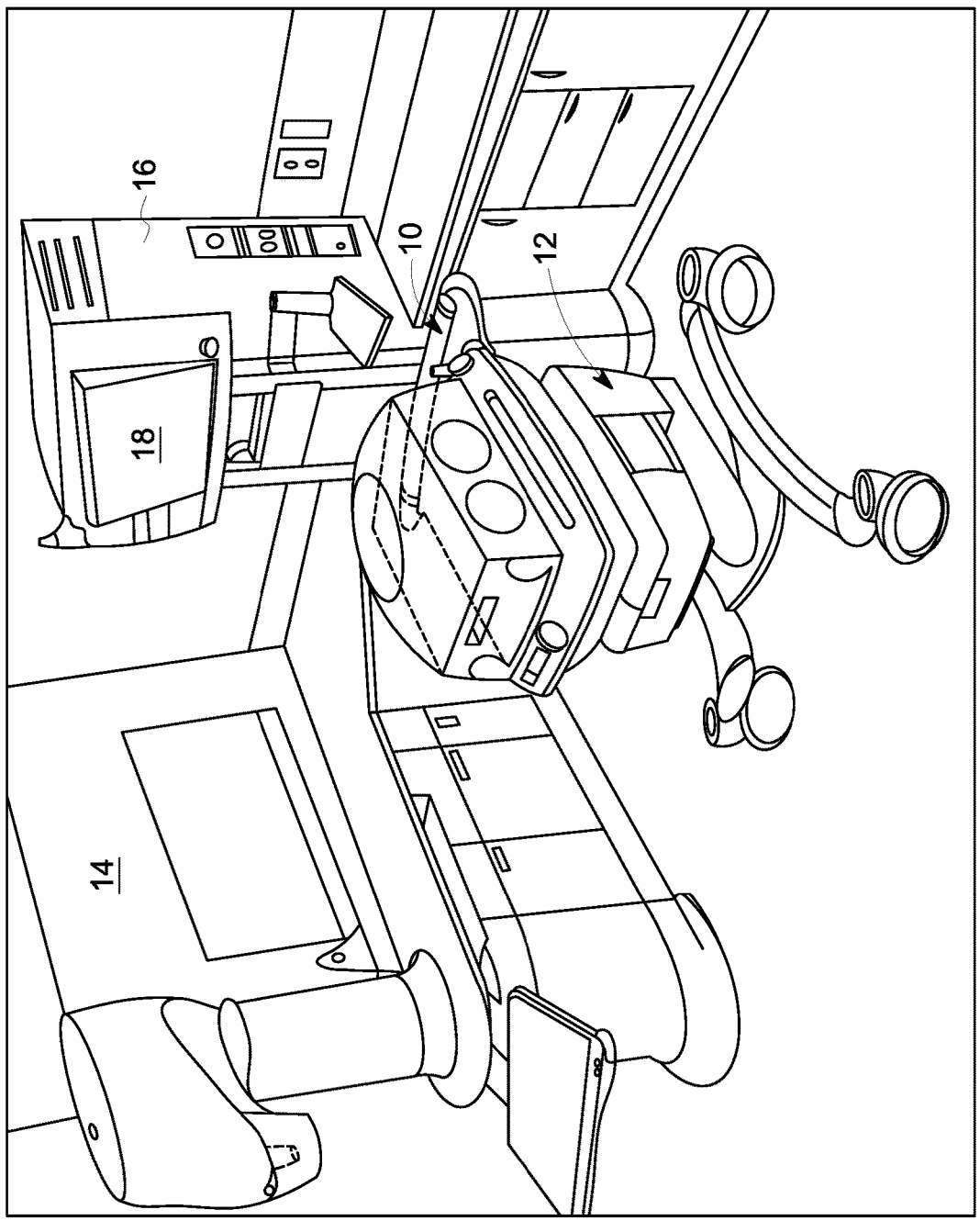
FIG. 1 is an environmental view that depicts an exemplary embodiment of an infant care station.

FIG. 1 depicts an environmental view of an infant care station 10. The infant care station 10 is depicted in this embodiment as an incubator; however, it will be recognized and understood from the disclosure and examples given herein that alternative embodiments of the infant care station 10 may include, but are not limited to, an incubator, a warmer and a hybrid warmer/incubator apparatus.

The infant care station 10 includes a mobile base 12 such that the infant care station 10 can be moved about a medical care facility, such as into a neonatal intensive care unit (NICU) 14. In the embodiment depicted in FIG. 1, the infant care station 10 is communicatively connected to a NICU workstation 16 that in embodiments provide additional functionality and data connections to the infant care station 10. The NICU workstation 16 can include a graphical display 18 that presents patient information to a clinician. As detailed herein, the graphical display 18 may be a touch-sensitive graphical display. In other embodiments, the graphical display 18 could be mounted to the infant care station 10.

Figure 2:
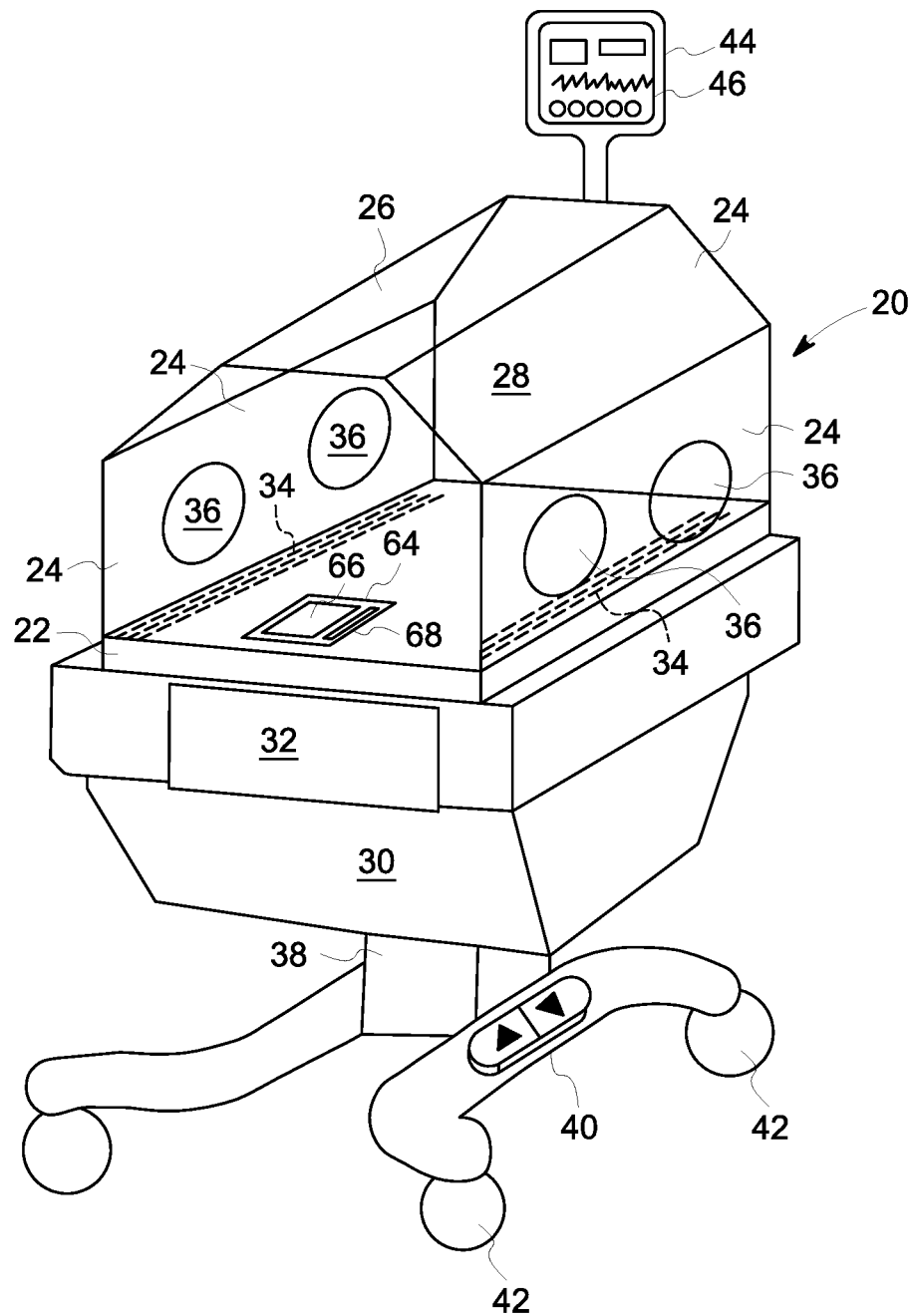
FIG. 2 exhibits an exemplary embodiment of an infant care station.

FIG. 2 depicts an exemplary embodiment of an infant care station in which the infant care station is an incubator 20. The incubator 20 includes a horizontal surface 22 that is configured to support an infant patient (not depicted). It is to be understood that the incubator 20 may have the ability or control to move, rotate, or incline the horizontal surface 22; however, it will be understood that the horizontal surface 22 will generally remain horizontal such as to minimize movement of the infant patient within the incubator 20 due to gravity.

One or more walls 24 extend generally vertically from the horizontal surface 22. In the embodiment depicted in FIG. 2 of the incubator 20, four walls extend vertically from the horizontal surface 22 to define the rectangular shape of the incubator 20. However, it will be understood that in alternative embodiments, various numbers of walls 24 may be used to define the incubator into various geometric shapes which may include, but are not limited to, circles or hexagons. The incubator 20 further includes a canopy 26 that extends over the horizontal surface 22. In some embodiments, as depicted in FIG. 2, the canopy 26 may include multiple components or surfaces, or, as depicted in FIG. 1, the canopy may be curved or domed in shape.

While the incubator of FIG. 2 is depicted with the horizontal surface 22, walls 24, and canopy 26 being integrally connected, it will be understood that in alternative embodiments, including those described in greater detail herein, the horizontal surface 22, walls 24, and canopy 26 may be individual components that also may be moveable with respect to each other.

The horizontal surface 22, walls 24, and canopy 26 define a microenvironment 28 contained within these structures. The incubator 20 is configured such that the microenvironment 28 surrounds the infant patient (not depicted) such that the infant patient is only exposed to a controlled combination of environmental conditions (temperature, humidity, $O_2$ concentration, etc.) selected by a clinician to promote the health and wellbeing of the infant patient.

The incubator 20 includes a base 30 that houses a convective heater 32. The convective heater 32 is operated such that air is drawn into the incubator 20, at which point the air may be filtered or sterilized in another manner, including the use of UV light before being passed by heating coils (not depicted) to heat the air to a target or set point temperature. The sterilized and heated air is blown into the microenvironment 28 through vents 34 which are arranged along the walls 24. As is also known, the air may be entrained with supplemental gasses such as oxygen or may have added humidity such as to control these conditions within the microenvironment 28.

The walls 24 further include arm ports 36 that permit a clinician access into the microenvironment 28. While facilitating clinician access to the microenvironment 28, the arm ports 36, or the hands/arms of the clinician reaching into the microenvironment 28 through the arm ports 36, can be a source of introducing bacterial or viral contamination into the microenvironment. This can create an infection risk to the infant patient. Therefore in use, a hospital or medical care facility may have sanitary requirements such as, but not limited to, washing with antibacterial soap, use of gloves or other forms of hand sanitizing by the clinician before accessing the microenvironment 28 through the arm ports 36. As previously described, some embodiments of the incubator 20 may align the vents 34 along the walls 24 in such a manner as to produce vertical jets of air along the walls 24. These vertical jets of air further create a barrier across the arm ports 36 against transmission of viral or bacterial contaminants through the arm ports 36 from outside the microenvironment 28. It has been observed that these requirements can present a problem to a clinician who accesses the microenvironment only to determine that an adjustment or control of an incubator feature or function is needed, requiring use of non-sterile control equipment.

Embodiments of the incubator 20 further include a pedestal 38 connected to the base 30. The pedestal 38 includes mechanical components (not depicted), which may include, but are not limited to, servo motors, rack and pinion systems, or screw gear mechanisms that are operable by foot pedals 40 to raise or lower the base 30, effectively raising or lowering the position of the infant patient (not depicted) in relation to the clinician. As previously disclosed, the incubator 20 may be moveable by wheels or casters 42 connected to the pedestal 38.

The exemplary embodiment of the incubator 20 depicted in FIG. 2 includes a graphical display 44 that is mounted to a wall 24 or the canopy 26 of the incubator 20 at a position external to the microenvironment 28. The graphical display 44 is operated by a processor to present a graphical user interface (GUI) 46. In the embodiment illustrated, the graphical display 44 is a touch-sensitive graphical display and the GUI 46 is configured to specifically respond to inputs made by a clinician received through the touch-sensitive graphical display. During normal operation, the touch-sensitive graphical display 44 and touch-sensitive configured GUI 46 are used to control various functions of the incubator 20. The GUI 46 presents a variety of information, such as the air temperature and alarm indications.

Non-limiting examples of the alarms that may be presented at 50 can include, but are not limited to, threshold indications for physiological parameters such as tachycardia, bradicardia, excessive or insufficient respiration rate, excessive or insufficient temperature or disconnection of a physiological monitoring sensor. The GUI 46 further presents a variety of controls such as, but not limited to, control of the air boost 54, which in an embodiment refers to the aforementioned jets of air provided along the walls 24 by the vents 34. The supplemental oxygen 56 operation of a scale function 60 and a presentation of measured patient trends 62.

In embodiments, the patient trends 62 may present various physiological measurements obtained from the infant patient over time. The physiological measurements may include, but are not limited to, temperature, respiration rate, nutrition, weight or other information as may be recognized by one skilled in the art.

Referring back to FIG. 2, an auxiliary input device 64 is located within the microenvironment 28. The auxiliary input device 64 solves the aforementioned problem of a clinician performing a sanitation procedure before accessing the microenvironment only to identify that a parameter change is required that requires operation of the touch-sensitive graphical display 44 in order to input such change to the touch-sensitive configured GUI 46. The auxiliary input device 64 can be activated by the clinician and, as described herein, the processor (not depicted) can change the function and operation of the GUI such that the clinician can interact with the GUI 46 through inputs and controls entered with the auxiliary input device 64.

In the embodiment depicted in FIG. 2, the auxiliary input device 64 includes a touch-sensitive track pad 66 and a button 68. It will be understood that this is a non-limiting example, and other embodiments of the auxiliary input device may include only a track pad, only a button, or multiple track pads and/or buttons. In embodiments, the track pad 66 may be a touch-sensitive panel that may or may not include an integrated graphical display and its own graphical user interface (not depicted). In still further embodiments, the auxiliary input device 64 may rather be an image capture device, such as a video camera (not depicted) that is operable to perform image captures of various clinician hand gestures that may serve as inputs to the processor in conjunction with the GUI 46.

Figure 6:
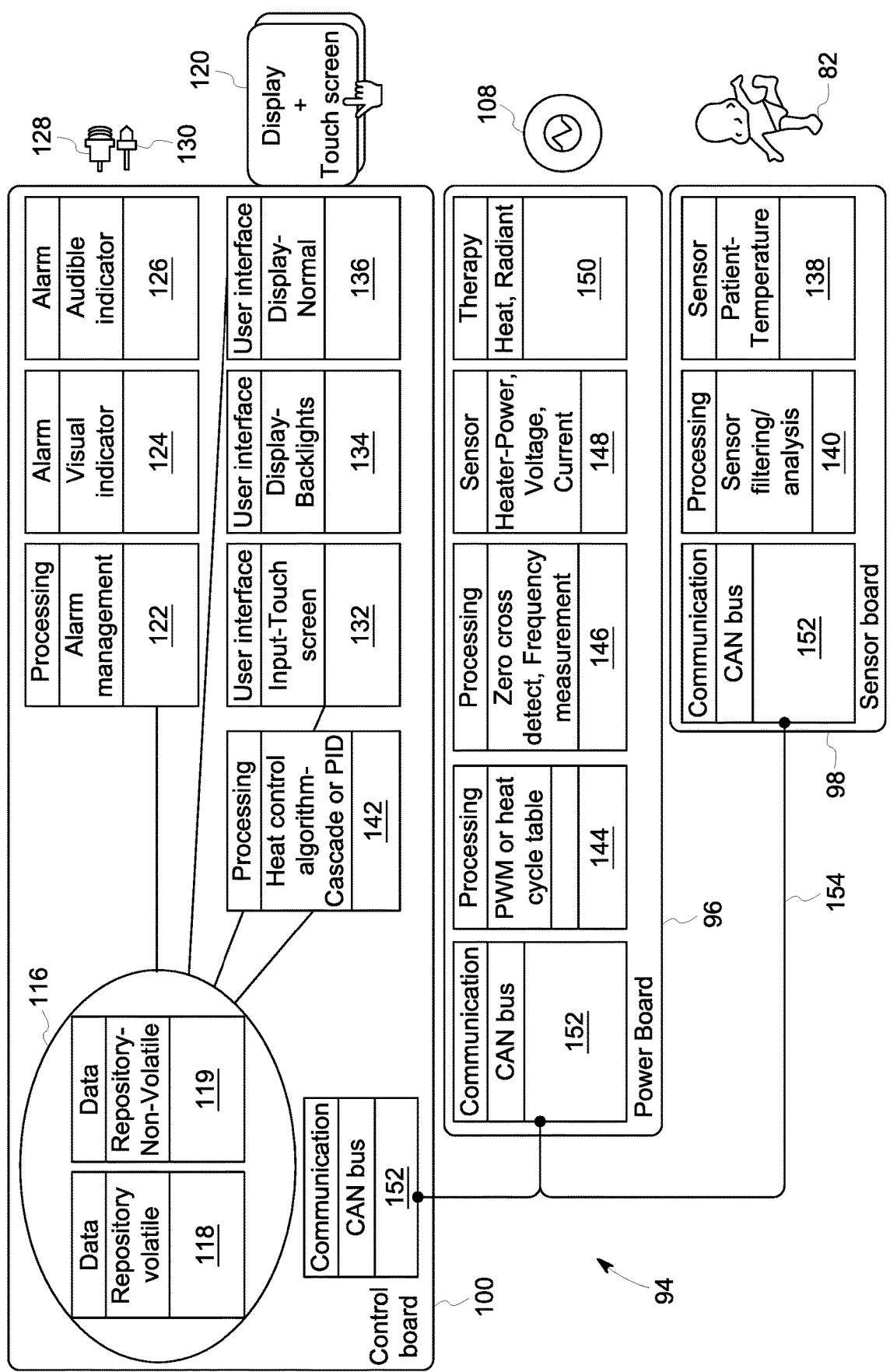
FIG. 6 is a physical block diagram of an exemplary infant care system.

As will be explained in further detail herein, the activation of the auxiliary input device 64 by the clinician may cause the processor to modify the GUI 46 presented on the graphical display 44, such that the GUI 46 is no longer configured for a touch-sensitive input, but rather presents a cursor 70 such as depicted in FIG. 6 that moves responsive to input commands provided at the auxiliary input device 64.

Figure 3:
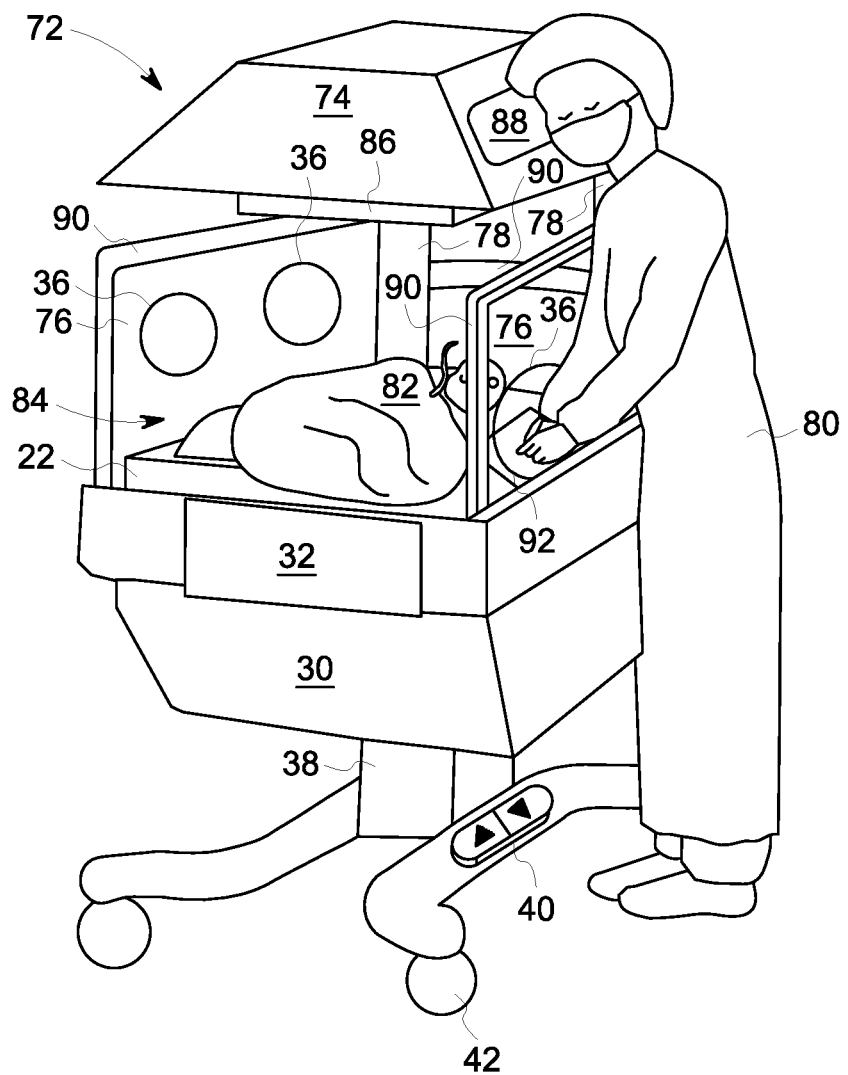
FIG. 3 depicts an alternate exemplary embodiment of an infant care station.

FIG. 3 depicts an alternative embodiment of an infant care station in which the infant care station is a hybrid infant care station 72 that can functionally operate as either a warmer or an incubator. In a hybrid infant care station 72, the canopy 74 is separate from the walls 76. The canopy 74 is vertically moveable with respect to the walls 76 and the horizontal surface 22 on vertical rails 78. The walls 76 include one or more arm ports 36 through which the clinician 80 can access the infant patient 82 located in the microenvironment 84 defined by the horizontal surface 22, walls 76, and canopy 74. It will be recognized that like reference numerals will be used between like structures found in FIGS. 2 and 3 in order to promote efficiency in the description.

The hybrid infant care station 72 is operable between incubator and warmer modes. When the hybrid infant care station 72 operates as a radiant warmer, the canopy 74 may be vertically separated along the rail 78 along the horizontal surface 22, and a radiant heater 86 located in the canopy 74 produces radiant heat energy that is directed downward at the infant patient 82, and thereby operates to control the temperature of the infant patient 82. When the hybrid infant care station 72 operates as an incubator, the canopy 74 is moved vertically closer to the horizontal surface 22 and the infant patient 82 thereby enclosing or partially enclosing the infant patient 82 in conjunction with the walls 76. In operation as an incubator, the hybrid infant care station 72 may control the temperature of the infant patient 82 with a convective heater 32, while in other embodiments, the convective heater 32 and the radiant heater 86 may work in conjunction in order to effectively control the temperature of the infant patient 82.

The embodiment of the hybrid infant care station 72 depicted in FIG. 3 includes a touch-sensitive graphical display 88 built into the canopy 74. The touch-sensitive graphical display 88 may operate in the manner as described above with respect to FIG. 2. It is also recognized that rather than being particularly located in the canopy 74, the touch-sensitive graphical display may alternatively be secured to the canopy rails 78 or a wall rail 90. However, in these instances, the touch-sensitive graphical display 88 is located outside of the microenvironment 84. Once the clinician 80 has gone through a sterilization procedure and is interacting with the infant patient 82 in the microenvironment 84, the clinician 80 can use the auxiliary input device 92 as described above, and as will be described in further detail herein, to input information and interact with a GUI presented on the touch-sensitive graphical display 88. As is shown in FIG. 3, the auxiliary input device 92 may be moveable within the microenvironment 84 such that the clinician 80 can move the auxiliary input device 92 to a convenient location or orientation for input use while still being able to attend to the infant patient 82.

Figure 4:
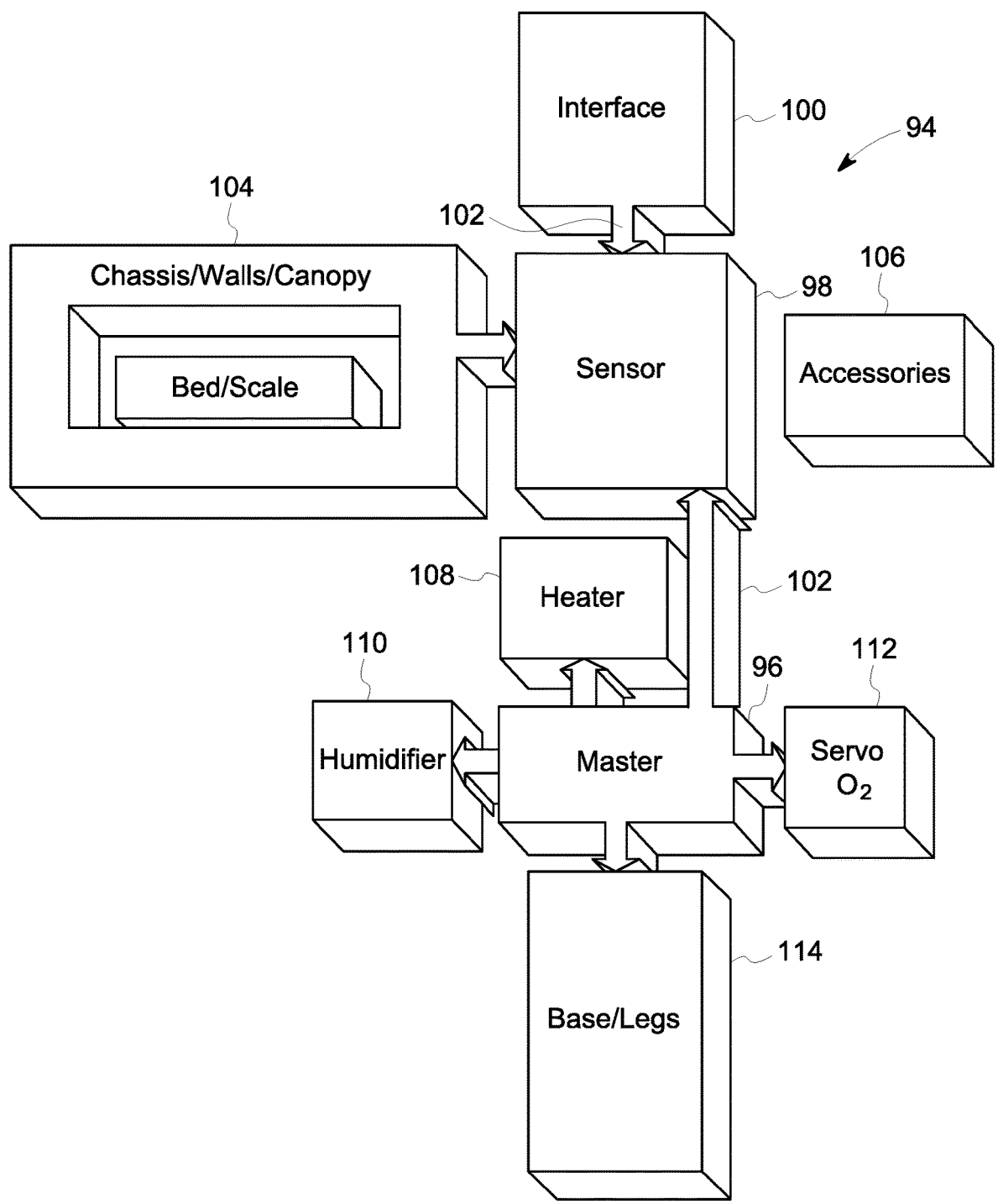
FIG. 4 is a schematic illustration of the interrelationship between the various modules of the infant care station.

As described above, the infant care station includes a number of sensing devices, operational components and displays whose functions must be coordinated to allow the infant care station to operate as desired. FIG. 4 provides a schematic illustration of a micro-environment platform 94 that coordinates the functions and activity of the infant care station and allows the infant care station to be upgradeable, scalable and easier to configure during manufacture. The micro-environment platform 94 shown in FIG. 4 includes three main modules that communicate with each other. Although three modules are shown in the embodiment of FIG. 4, it should be understood that additional modules could be added and utilized while operating within the scope of the present disclosure.

The three main modules included as part of the micro-environment platform 94 include a master module 96, a sensor module 98 and an interface module 100. As illustrated in the embodiment of FIG. 4, each of the three modules are connected to a universal interface bus 102 and are able to communicate with each other over the universal interface bus 102, the details of which will be discussed in much greater detail below. The communication between the three separate modules 96, 98 and 100 over the universal interface bus 102 allows each of the separate modules to easily communicate with each other to coordinate functions, data transfer and power connections.

It is contemplated that all of the functions required by the infant care station, whether the infant care station is an incubator, a warmer or a hybrid device, can be implemented using the three modules shown in FIG. 4. The assignment of various functions to each of the three modules 96, 98 and 100 is based upon the physical location of the function, functional commonality between individual functions assigned to each module and data sharing requirements. This type of cohesiveness for functions carried out by each of the modules will provide improved performance. In the embodiment shown in FIG. 4, the interface module 100 provides user interface functions, including information display, user controls, alarms, indicators, external communication and other similar functions. The sensor module 98 is designed as a module that provides the monitoring connections for patient physiological sensors, including all of the sensors contained within the chassis, walls and canopy of the infant care system, as shown by reference numeral 104. These parameters can include the temperature, weight and $SpO_2$ readings from the infant patient while also including environmental sensors that detect conditions within the micro-environment, including temperature, humidity and oxygen concentration. The sensor module 98 can also communicate to various different monitoring accessories 106 as desired.

The third module, referred to as the master module 96, provides the control of therapy devices and movement motors within the infant care stations. These therapy functions may be a radiant heater 108, a humidifier 110, oxygen servo motors 112 as well as the lift motors 114 used to adjust the height of the infant platform. The master module 96 can control a wide variety of other functions, as will be further described below.

Figure 5:
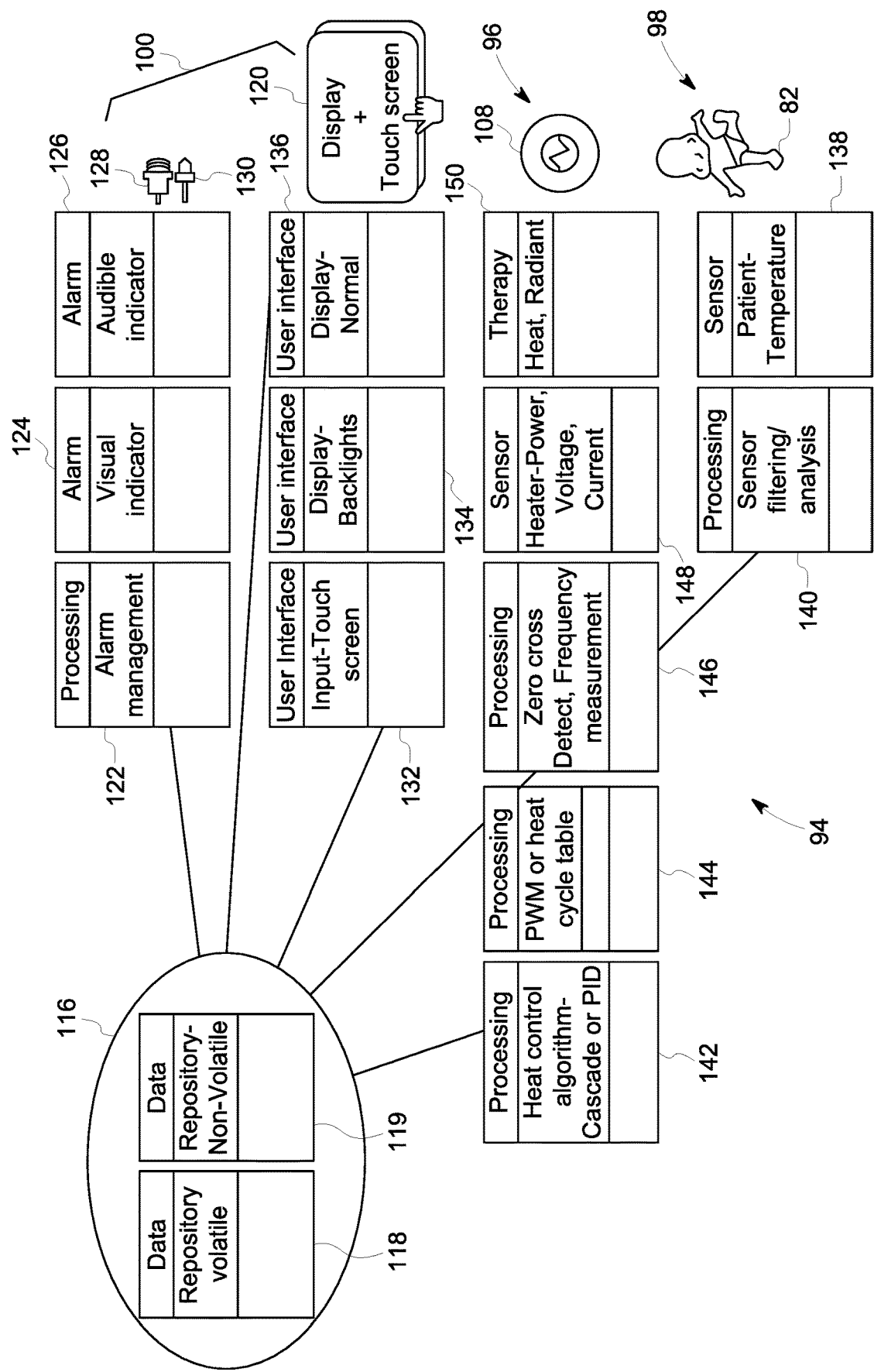
FIG. 5 is a functional block diagram of an exemplary infant care station.

FIG. 5 provides a functional block diagram for the micro-environment platform 94 of the present disclosure. As described previously, the micro-environment platform 94 includes the three separate modules 96, 98 and 100 that coordinate to carry out all of the functions required by the infant care station. In accordance with the present disclosure, the micro-environment platform 94 further includes a data repository 116. The data repository 116 is a shared access memory location for all data parameters that are required for operation and for measured data obtained from various sensing devices in the infant care station. As illustrated in FIG. 5, the data repository 116 can include both volatile memory 118 and nonvolatile memory 119. A data producer, such as various sensors located within the infant care station, can write data to the data repository 116 as required. Data subscribers, such as the display 120, can read the same data stored within the data repository 116 as needed. The data repository 116 can hold trend data, device configuration data, operating algorithms, patient data as well as real-time control data.

As illustrated in the functional block diagram of FIG. 5, a processing function of the interface module 100 can retrieve sensor information and alarm parameters from the data repository 116. Based upon the retrieved alarm parameters and sensor information, the processing function 122 can generate a visual alarm in block 124 and an audible alarm in block 126. The audible alarm is played through speaker 128 while the visual alarm can be indicated through an indicator light 130.

The interface module 100 can further include a user interface, such as the touchscreen display 120 that relays inputs to the processing block 132. Based upon inputs from the touchscreen display 120, the user can adjust the intensity of a display screen through block 134, which is carried out in block 136. In addition, the interface module 100 can receive mode selection information from the user. For example, if the infant care station is an incubator, the incubator can be operated in different modes, such as an "air mode" or a "baby mode". In the air mode, the temperature within the incubator is controlled to a user set point. In the baby mode, the temperature is controlled to a desired temperature of the baby, which is detected by a patient probe. The mode selection and temperature set points are all stored in the data repository 116. Similar modes of operation are available for an infant warmer and hybrid device.

The sensor module 98 can include a wide variety of sensors used to monitor the current status of the infant patient 82 or the micro-environment. In the embodiment shown, the system includes a temperature sensor 138. In accordance with the present disclosure, the input signals obtained from the infant patient 82 by the temperature sensor 138 can be filtered in operational block 140. It is contemplated that the results of the filtering and analysis block 140 are configured using a standard data format standard such that the information obtained from the patient temperature sensor 138 can be stored in the data repository 116 in the standard data format. The standard data format allows the interface module 100 to retrieve the patient temperature information for display on the display 120. By formatting the information obtained from the patient 82 in a standard data format, any data subscriber in the infant care station can obtain the information from the data repository and use the information as needed.

As an illustration, the master module 96 includes a processor that retrieves a heat control algorithm from the data repository 116, as illustrated by block 142. The master module 96 would also retrieve information about the selected operating mode and temperature set points from the data repository 116. For example, when the incubator is in the "air mode", the master module 96 utilizes the air temperature in the incubator to control the operation of the heating element. When the incubator is in the "baby mode", the master module utilizes the baby temperature from the patient probe to control the operation of the heating element.

In block 144, the processor of the master module 96 retrieves PWM information or a heat cycle table from the data repository 116. In functional block 146, the processor of the master module 96 determines other operational functions of the heater while sensor information related to the operation of the heater is obtained in block 148. Based upon this information, the master module 96 provides power to a radiant heater 108 in step 150. As can be understood, in order for the master module 96 to operate the radiant heater 108 properly, the master module 96 must retrieve sensor information related to the patient temperature for the data repository 116. Based upon this information retrieved from the data repository 116, the sensor module 96 is able to accurately operate the radiant heater.

FIG. 6 provides one embodiment of the physical locations of the functional blocks illustrated in FIG. 5. The physical block diagram shown in FIG. 6 is meant to illustrate one physical implementation of the multiple modules used in the infant care station constructed in accordance with the present disclosure. Other physical configurations are contemplated as being within the scope of the present disclosure.

As illustrated in FIG. 6, the data repository 116 is shown as part of the interface module 100. Since the interface module 100 provides most of the user interface functions, it is contemplated that locating the data repository 116 in this location would provide the most efficient location for the data repository. However, it is contemplated that the data repository 116 could be located as part of either the sensor module 98 or the master module 96.

Each of the individual modules includes a communication application 152 that allows the individual modules 96, 98 and 100 to communicate with each other. Each of the communication applications 152 configure communication messages for communication over a CAN bus 154. The CAN bus 154 is a standard communication bus that allows microcontrollers and devices to communicate with each other in various different types of applications that do not require a host computer. The CAN bus 154 is a message-based protocol. The CAN bus 154 allows for each of the individual modules to communicate with each other and to retrieve and store data onto the data repository 116. The CAN bus 154 forms a part of the universal interface bus 102 shown between the various modules in FIG. 4. The other portions of the universal interface bus 102 will be described with reference to FIG. 7.

FIG. 7 illustrates a more detailed electrical schematic illustration of the separate modules that form the infant care station. As illustrated, the micro-environment platform 94 includes the master module 96, the sensor module 89 and the interface module 100. In the embodiment shown in FIG. 7, the interface module 100, the sensor module 98 and the master module 96 are all connected to the universal interface bus 102. The universal serial bus 102 allows all of the modules to communicate with each other and be connected in a daisy chain format. The modules can also utilize the universal interface bus 102 to communicate externally to a management or testing station 156. In the embodiment illustrated, the universal interface bus 102 is referred to as a LINCAN tunnel. The LINCAN tunnel includes the CAN bus 154 shown in FIG. 6, an LIN bus, a power connection and a control connection. The LIN bus is a low speed, low priority serial network protocol that is used for communication between various components. The LIN bus is an inexpensive, serial communications protocol used to communicate between one of the processors and external components.

The power connections contained as part of the universal interface bus 102 include a 24-volt main DC power supply line that provides up to 4 amps of current. The power connection also includes a 5-volt DC standby power supply line that can be used to operate the microprocessors contained on each of the modules as well as various different components connected to the microprocessors upon loss or interruption of the main power supply line. The universal interface bus 102 thus provides all of the power and communication pathways needed for each of the processors and devices contained on and connected to the various modules 96, 98 and 100. The modules are able to communicate with each other as well relay commands and receive information from the devices associated with each of the modules over the universal interface bus 102.

Figure 7A:
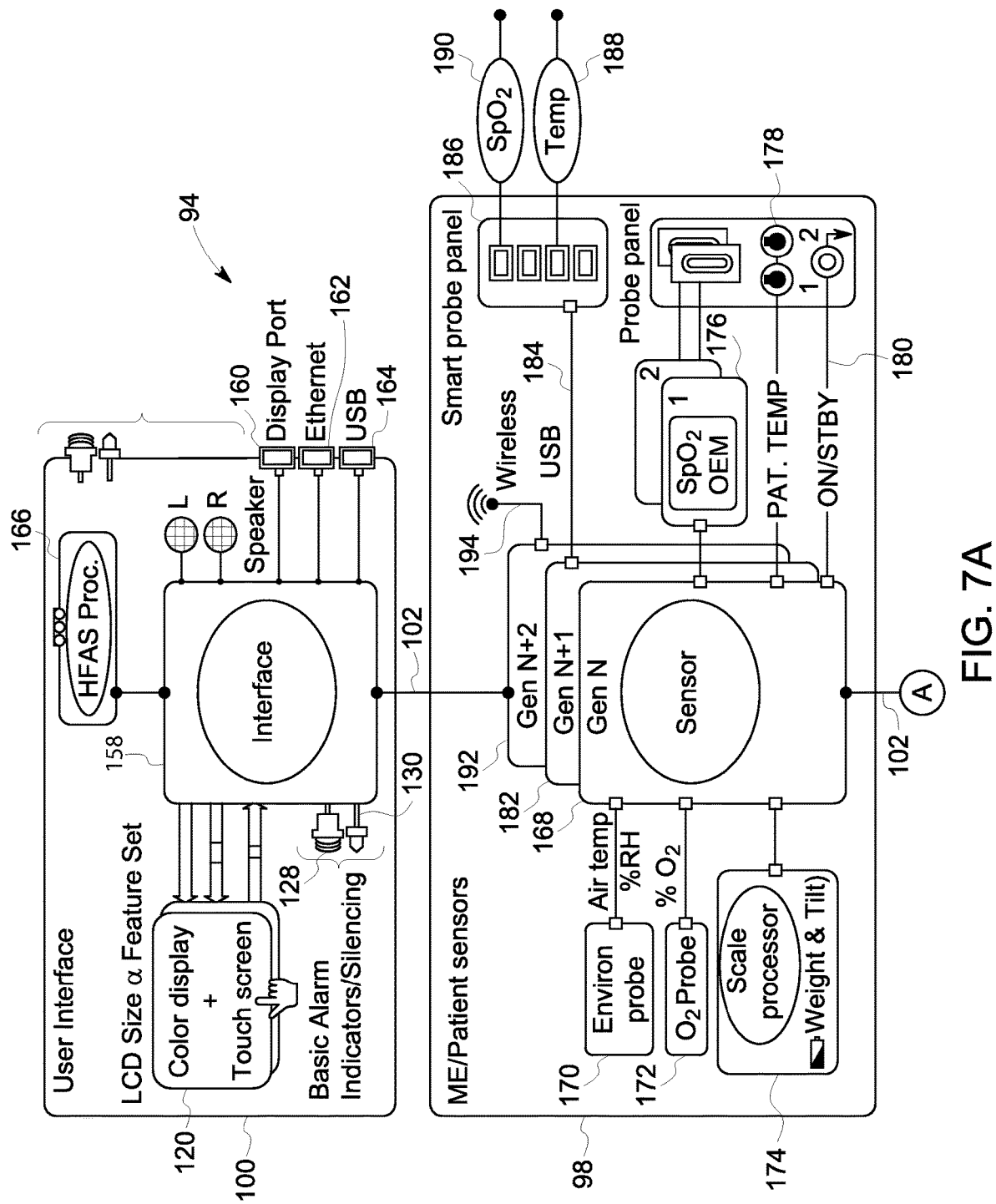
FIGS. 7A and 7B are a schematic illustration of the electrical platform of an exemplary embodiment of the infant care station.
Figure 7B:
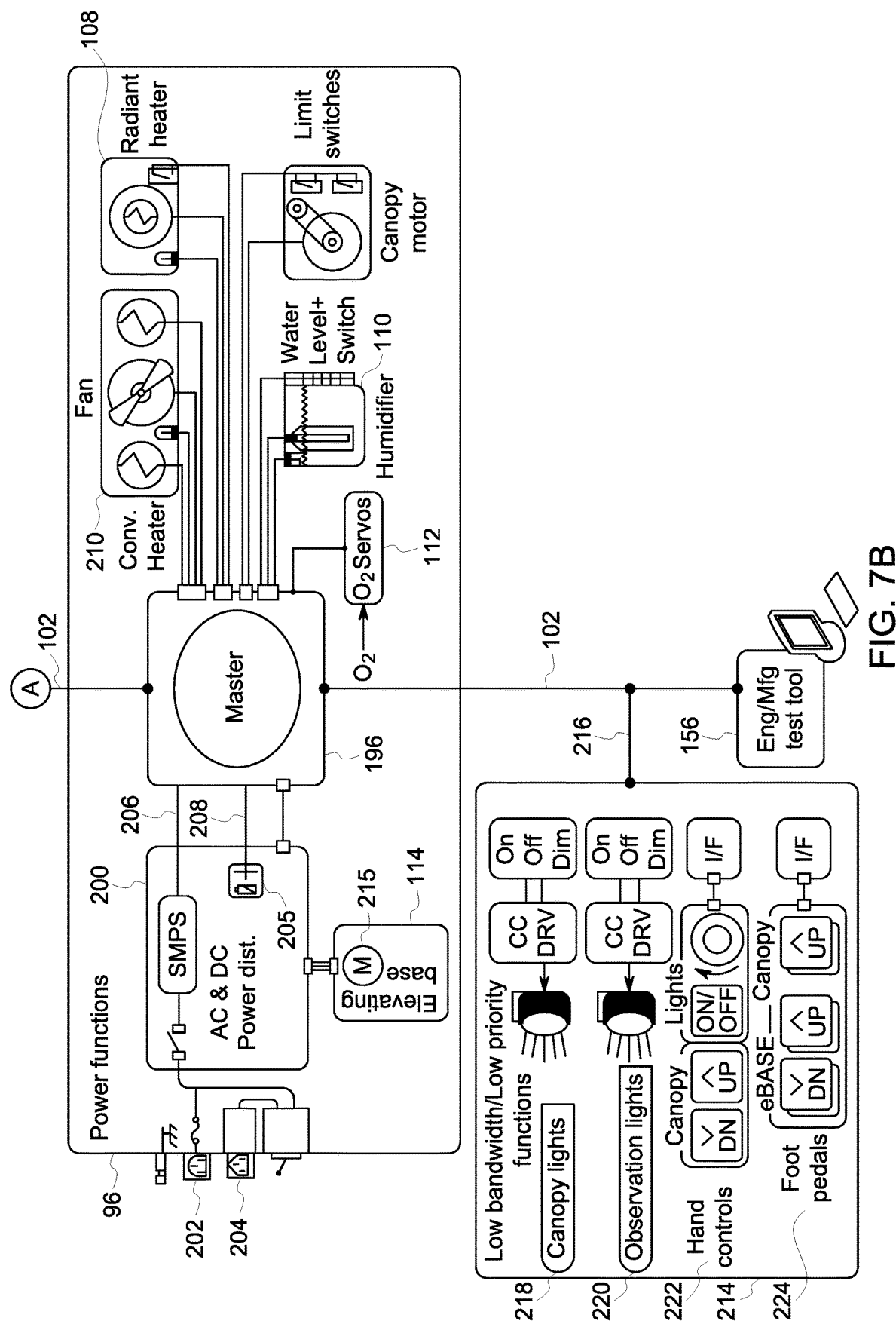

The electrical platform illustration shown in the combination of FIGS. 7A and 7B illustrates all of the requirements and options for each of the individual modules for the micro-environment platform 94 when being used in an application of an incubator, warmer or a hybrid device. It is contemplated that various different components may not be needed when the micro-environment platform 94 is utilized with different types of infant care stations. As an example, when the micro-environment platform 94 is utilized with an infant warmer, many of the operation devices included as part of the master module 96 would not be utilized.

The interface module 100 is shown including a primary processor 158 that receives a series of inputs and generates a series of outputs. The processor 158 communicates with the display 120 to present images and data to an operator while also receiving user inputs from the touchscreen. The processor 158 can include multiple input/output ports, such as the display port 160, an Ethernet port 162 and a USB port 164. These series of ports allow for different types of configurations for the micro-environment platform 94. The processor 158 is further connected to an alarm processor 166 that controls the operation of visual alarm indicators (LEDs of different colors depending on alarm priority), power fail indicators, and hands-free alarm silence functions. The interface module 100 is also able to control additional speakers in an enhanced manner.

The sensor module 98 is shown in FIG. 7A as including a first generation (Gen N) processor 168. The first generation processor 168 receives information from an environmental probe 170, an oxygen probe 172, a scale processor 174, an SpO$_2$ monitor 176 and a patient temperature monitor 178. The sensor module 98 includes an auxiliary input 180 that can be connected to other types of patient sensors. The first generation processor 168 receives all of the information from the various sensors and communicates this sensor information to the data repository 116 as shown in FIGS. 5 and 6. Although the data repository 116 is not shown in the embodiment of FIGS. 7A and 7B, it should be understood that the data repository 116 could be located on the interface module 100.

When the processor 168 receives the sensor input from the various different sensing devices, the processor 168 utilizes a standard data format for configuring the sensor information. The standard data format ensures that all of the sensor information is transformed into a standard format such that the sensor data can be stored in the data repository 116. If all of the sensor data is stored utilizing the standard data format, each of the modules can then retrieve the sensor data and utilize the sensor data as needed. By utilizing a standard data format, various different sensor modules can be easily removed, replaced and upgraded without affecting the operation of the rest of the micro-environment platform.

As an illustrative example, a Gen N+1 processor 182 is shown in FIG. 7A. The processor 182 is meant to represent the next generation of sensing devices. As shown, the processor 182 is connected by a USB cable 184 to a smart probe panel 186, which in turn is connected to an advanced temperature sensor 188 and an advanced SpO$_2$ sensor 190. The advanced temperature sensor 188 and SpO$_2$ sensor 190 include additional processing power on the sensors themselves such that the signals from the enhanced temperature sensor 188 and SpO$_2$ sensor 190 are filtered and processed before being relayed to the processor 182 through the USB cable 184. A Gen N+2 processor 192 is meant to represent an even more advanced sensor network. The Gen N+2 processor 192 includes a wireless transceiver 194 that is able to communicate to one or more wireless sensors that are positioned on the infant patient or within the micro-environment. The wireless sensors represent the newest type of patient monitoring and can be worn on the infant patient without any wired connections to a monitoring processor.

The universal interface bus 102, data repository 116 and common data standard allows the sensor modules 98 to be easily removed and replaced to upgrade the micro-environment platform 94. Since each of the modules 96, 98 and 100 are separate, distinct components, each of the modules could be removed and replaced without affecting the operation of the remaining modules.

The master module 96 includes a master processor 196. The master processor 196 is connected to a power circuit 200 that receives a supply of AC power through an input 204. Input 204 includes a filter and circuit breaker and is connected to an output receptacle 202 through a fuse. The power circuit 200 converts the AC power input to the 24-volt DC main power supply line 206. The power circuit 200 further includes a battery or super capacitor shown collectively at 205 that serves as the 5-volt standby power supply when the AC power input is interrupted or otherwise becomes unavailable. The battery or super capacitor 205 are charged when the AC power input is present and discharge when the AC power input is not available. The standby power is used to power critical components of the infant care station when the AC power input is not available. The multiple power supplies are provided to the master processor 196 through the DC main voltage supply line 206 and a low voltage standby power supply line 208. The master processor 196 provides these two voltage values to the universal interface bus 102 as described above. The master processor 196 is used to provide the required power to operate various different components of the infant care station. As discussed previously, one of the components is a radiant heater 108. The radiant heater 108 is commonly used in the infant warmer embodiment. A convection heater 210 can be utilized in other applications, such as an incubator. The convection heater 210 includes heating elements and a fan to circulate the heated air throughout the micro-environment. A humidifier 110 can also be controlled by the master processor 196. Oxygen servo motors 112 can further be operated by the master processor 196. Motor 215 can be operated to raise and lower the base of the infant care station and is connected directly to the power circuit 200.

As can be understood in FIG. 7B, the master module 96 is used to supply power to the various operating components of the infant care station. The master module 96 will typically be located near the bed and close to both the power inputs and all of the motors/heating elements that are required by the infant care station. The sensing module 98 will typically be located near the patient since the sensing module is physically connected to sensors that monitor both the patient and the micro-environment. The interface module 100 will typically be located near the display since much of the operation of the interface module 100 is dictated by the display 120.

In the embodiment shown in FIG. 7B, the three modules can communicate with a series of low priority controls 214 through just the LIN bus 216. Only the LIN bus 216 is used to communicate to the low priority controls 214 since the controls are relatively simple devices that provide simple signals, such as on/off or up/down. The low priority controls 214 are used to control various low priority functions, such as the canopy lights 218, observation lights 220, the hand controls 222 and the foot pedals 224. These various different components, while useful and needed on the infant care station, are able to communicate with the master controller 196 utilizing the low speed, low priority LIN bus 216 that is included in the universal interface bus 102. The low priority controls 214 can be located a different physical locations on the infant care station and can communicate with one or multiple of the modules.

Figure 8:
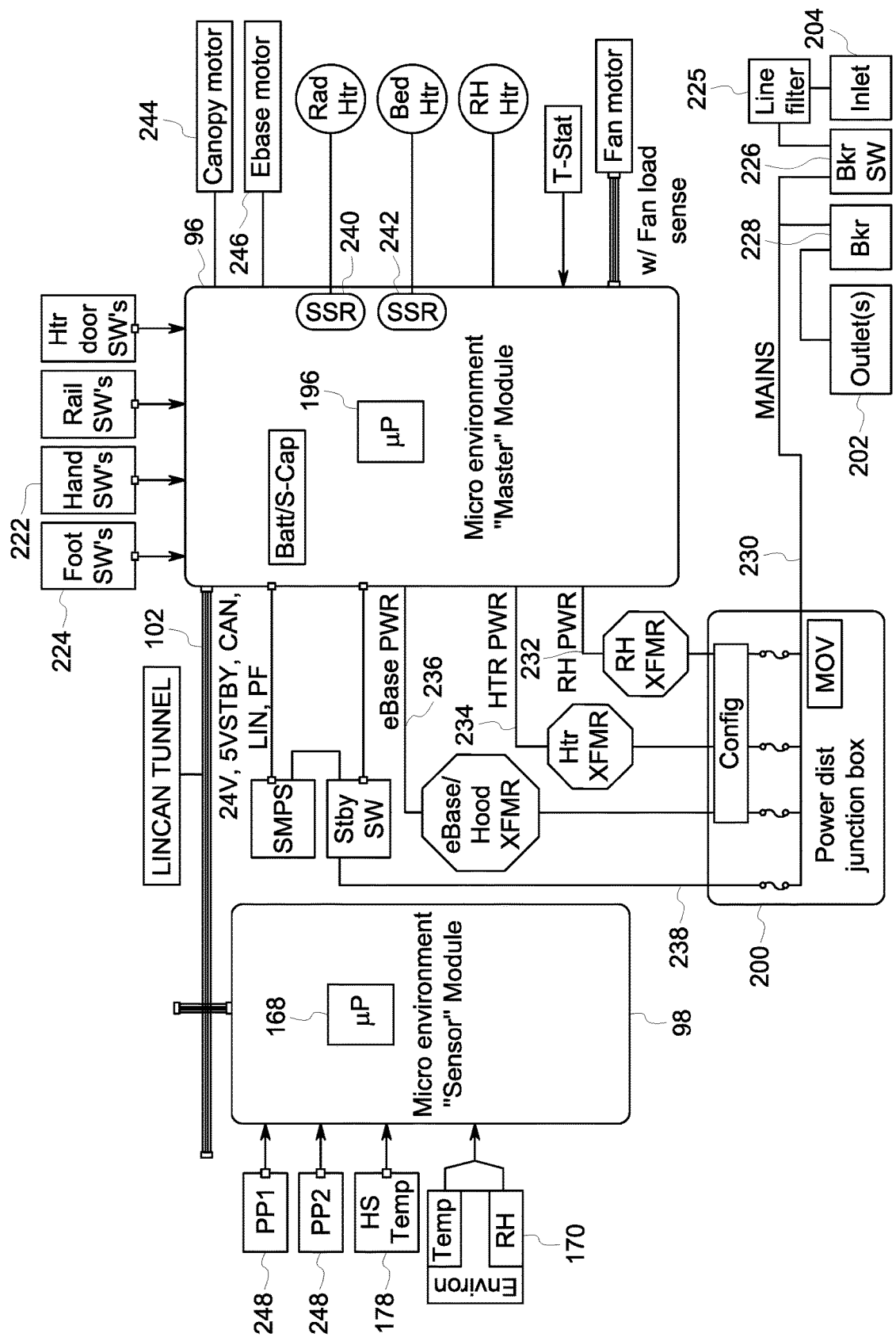
FIG. 8 is a schematic illustration of the electrical connections within the exemplary embodiment of the infant care station.

FIG. 8 provides a further detailed view of the connections to the master module 96 and the sensor module 98. As discussed in FIG. 7, the master module 96 is connected to the power circuit 200, which is a distribution junction box in the embodiment shown. The power circuit 200 receives AC power input from the input 204, which is connected to a filter 225 and a circuit breaker 226. The output receptacle 202 is connected to a separate breaker or fuse 228. The AC input along line 230 creates multiple power outputs. One of the power outputs 232 is used to drive the radiant heater, while power output 234 is used to drive the convection heater. Power output 236 is used to control the base of the infant care station while output 238 creates a source of standby power and a 5-volt DC power supply. The master processor 196 can control the position of a series of relays 240, 242 to supply power to the various heating elements. The processor is also able to control a canopy motor 244 and a base motor 246. The master processor 196 receives input from the foot pedal switches 224, the hand control switches 222 as well as other switches utilized by the operator.

The master module 96 provides the power lines to the universal interface bus 102 and communicates to the interface module (not shown) and sensor module 98 through the universal interface bus 102. The sensor module 98 includes the processor 168 as well as a series of patient probes 248, the environmental probe 170 and the temperature sensor 178.

The universal interface bus 102 is an eight pin connection, which reduces the number of connections and wires needed to communicate between the sensor module 98 and the master module 96.

This written description uses examples to disclose the invention, including the best mode, and also to enable any person skilled in the art to make and use the invention. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

We claim:
1. An infant care station that creates a micro-environment for an infant patient, comprising:
   a data repository configured to receive and store sensor input signals in a standard data format;
   a universal interface bus including a DC main power supply line, a low voltage standby power supply line, a high priority communication bus and a low priority communication bus;
   an interface module connected to the universal interface bus and including a display and a plurality of input ports, wherein the interface module communicates with the data repository through the universal interface bus to retrieve the sensor input signals;
   a plurality of sensor module in communication with the data repository and the interface module over the universal interface bus, the plurality of sensor modules each receiving sensor input signals from at least one sensor positioned to detect at least one parameter related to the infant patient or the micro-environment, wherein each of the plurality of the sensor module can be separately connected and disconnected from the universal interface bus and each of the sensor modules configures the sensor input signals for storage in the standard data format; and
   a master module in communication with the plurality of sensor module, the data repository and the interface module over the universal interface bus, the master module being operable to retrieve the sensor input signals from the data repository and operable to control at least one power output to control at least one power device of the infant care station.

2. The infant care station of claim 1 wherein the high priority communication bus is a CAN bus.

3. The infant care station of claim 1 wherein the low priority communication bus is a LIN bus.

4. The infant care station of claim 1 wherein the master module receives an AC power supply and converts the AC power supply to an operational power supply to activate a plurality of power devices of the infant care station.

5. An infant care station that creates a micro-environment for an infant patient, comprising:
   a data repository configured to receive and store sensor input signals in a standard data format;
   a universal interface bus including a DC main power supply line, a low voltage standby power supply line, a high priority communication bus and a low priority communication bus;

an interface module connected to the universal interface bus and including a display and a plurality of input ports, wherein the interface module communicates with the data repository through the universal interface bus to retrieve the sensor input data;

a sensor module in communication with the data repository and the interface module over the universal interface bus, the sensor module receiving at least one sensor input signal from at least one sensor positioned to detect at least one parameter related to the infant patient or the micro-environment and to configure the sensor input signal for storage in the standard data format; and a master module in communication with the sensor module, the data repository and the interface module over the universal interface bus, the master module being operable to retrieve the sensor input signals from the data repository and operable to control at least one power output to control at least one power device of the infant care station;

wherein the sensor module can be replaced with an updated sensor module, wherein the updated sensor module configures the sensor input signals for storage in the data repository according to the standard data format.

6. The infant care station of claim 5 wherein the data repository is configured to store operating parameter for the master module, the interface module and the sensor module.

7. The infant care station of claim 5 wherein the data repository is contained on the interface module.

8. The infant care station of claim 5 wherein the high priority communication bus is a CAN bus.

9. The infant care station of claim 5 wherein the low priority communication bus is a LIN bus.

10. The infant care station of claim 5 wherein the master module receives an AC power supply and converts the AC power supply to an operational power supply to activate a plurality of power devices of the infant care station.

11. An infant care station that creates a micro-environment for an infant patient, comprising:

a data repository configured to receive and store sensor input signals, alarm parameter and other data parameters;

a universal interface bus including a DC main power supply line, a low voltage standby power supply line, a high priority communication bus and a low priority communication bus;

an interface module including a display, an input device and at least one communication port, the interface module being in communication with the universal interface bus such that the interface module communicates with the data repository through the universal interface bus to retrieve the sensor input data;

a sensor module in communication with the data repository over the universal interface bus, the sensor module receiving at least one sensor input signal from at least one sensor positioned to detect at least one parameter related to the infant patient or the micro-environment, wherein the sensor module conditions the sensor input signal according to the standard data format; and a master module in communication with the data repository over the universal interface bus, the master module receiving a power supply and operable to generate at least one power output to control at least one power device of the infant care station based on retrieved sensor input signals, the master module being operable to retrieve the sensor input signals from the data repository;

wherein the interface module, the sensor module and the master module all have access to the data repository through the universal interface bus.

12. The infant care station of claim 11 wherein the high priority communication bus is a CAN bus.

13. The infant care station of claim 11 wherein the low priority communication bus is a LIN bus.

14. A micro-environment platform for interconnecting multiple modules of different types of infant care stations including at least an incubator, an infant warmer and a hybrid device that each create a micro-environment for an infant patient, comprising:

a data repository configured to receive and store sensor input signals in a standard data format;

a universal interface bus including a DC main power supply line, a low voltage standby power supply line, a high priority communication bus and a low priority communication bus;

an interface module connected to the universal interface bus and including a display and a plurality of input ports, wherein the interface module communicates with the data repository through the universal interface bus to retrieve the sensor input data;

a sensor module in communication with the data repository and the interface module over the universal interface bus, the sensor module receiving at least one sensor input signal from at least one sensor positioned to detect at least one parameter related to the infant patient or the micro-environment and to configure the sensor input signal for storage in the standard data format; and a master module in communication with the sensor module, the data repository and the interface module over the universal interface bus, the master module being operable to retrieve the sensor input signals from the data repository and operable to control including at least one power output to control at least one power device of the infant care station, wherein the interface module, the sensor module and the master module all have access to the data repository through the universal interface bus.

* * * * *